United States Patent
Bodmeier et al.

(12) 
(10) Patent No.: US 6,169,130 B1
(45) Date of Patent: Jan. 2, 2001

(54) METHOD FOR IMPROVING THE DISPERSION OF REDISPERSIBLE POLYMER POWDERS

(76) Inventors: Roland Bodmeier, Ravenberg 18, 14163 Berlin (DE); James W. McGinity, 4209 Dunning La., Austin, TX (US) 78746

( * ) Notice: Under 35 U.S.C. 154(b), the term of this patent shall be extended for 0 days.

(21) Appl. No.: 09/316,815

(22) Filed: May 21, 1999

(30) Foreign Application Priority Data

May 24, 1998 (DE) .............................................. 198 24 650

(51) Int. Cl.$^7$ .............................. C08K 7/16; C08K 5/41; C08L 1/00
(52) U.S. Cl. .................... 523/334; 523/333; 523/223; 524/35; 524/156
(58) Field of Search .................... 523/223, 333, 523/334; 524/35, 156

(56) References Cited

U.S. PATENT DOCUMENTS

| | | | |
|---|---|---|---|
| 4,849,227 | * | 7/1989 | Cho ....................................... 424/498 |
| 5,403,894 | * | 4/1995 | Tsai et al. ............................. 525/285 |
| 5,777,003 | * | 7/1998 | Haas et al. ............................ 523/223 |
| 6,046,277 | * | 4/2000 | Kolter et al. .......................... 525/205 |

OTHER PUBLICATIONS

Thomas A. Wheatley and Carl R. Steuernagel, "Latex Emulsions for Controlled Drug Delivery," *Aqueous Polymeric Coatings for Pharmaceutical Dosage Forms*, vol. 79, 1997, pp. 1–54.

* cited by examiner

*Primary Examiner*—Kriellion Sanders
(74) *Attorney, Agent, or Firm*—Rick Matos; Innovar, L.L.C.

(57) ABSTRACT

The method according to the present invention includes the step of adding sufficient amounts of an alkalinizing agent to an aqueous solution into which a redispersible polymer powder will be dispersed or to an aqueous dispersion which will be dried to form a redispersible polymer powder. The method of the invention is particularly well suited for nonionic polymers. A surfactant, plasticizer and/or preservative can also be used in addition to the alkalinizing agent. Redispersible polymer powders processed according to the invention form acceptable tablet coatings which are comparable in quality to those coatings formed from aqueous polymer dispersions that have not been dried into redispersible polymer powders.

20 Claims, No Drawings

METHOD FOR IMPROVING THE DISPERSION OF REDISPERSIBLE POLYMER POWDERS

FIELD OF THE INVENTION

This invention relates to a method for improving the dispersion of redispersible polymer powders into a solution. In particular, the invention is a method of dispersing redispersible polymer powders, wherein the polymer powders are dispersed into an aqueous solution containing an alkalinizing agent.

BACKGROUND OF THE INVENTION

Dosage forms having an extended drug release profile are manufactured by different industries, including in particular the pharmaceutical and chemical industry. For example, for the treatment of certain diseases, it is advantageous to administer the drug in an extended release form. The use of dosage forms with extended drug release normally leads to a better control of the drug release and therefore of the blood levels, to a reduction in the frequency of dosing and to a lower total drug dose. With these extended drug release systems, the drug is released either at a constant or at a decreasing rate over an extended period of time.

Dosage forms with extended drug release are prepared by coating solid drugcontaining dosage forms, like tablets or pellets, with polymer solutions or -dispersions. The polymer coating forms the diffusion barrier and retards the drug release. The polymers, in either organic or aqueous systems, are coated onto the dosage form in pans or fluidized bed equipment. Organic polymer solutions generally yield films of acceptable quality; however, the use of organic solvents in the pharmaceutical industry is problematic and is not preferred due to environmental, toxicity, explosion hazards, and residual solvent concerns.

Aqueous polymers dispersions instead of organic polymer solutions are, therefore, generally preferred for coating solid dosage forms. In aqueous polymer dispersions, the polymer is finely dispersed in water. The film formation from aqueous polymer dispersions occurs after the evaporation of water during the coating process through coalescence (fusion) of the polymer particles at temperatures above the minimum film formation temperature (MFT) in an ideally homogeneous film.

Polymer dispersions are two-phase systems, consisting of a dispersed colloidal polymer phase and an aqueous phase, which is the dispersion vehicle. The techniques for the preparation of polymer dispersions are either emulsion polymerization with water-insoluble monomers (latex-dispersions) or physical preparation methods, which use an already synthesized polymer. In the latter technique, a polymer solution or -melt is emulsified and homogenized in an aqueous phase. The polymer dispersion is obtained after evaporation of the solvent or cooling of the aqueous phase to form a pseudo-latex dispersion.

Acrylic polymers (for example, Eudragit™ polymers) or cellulose derivatives are frequently used as water-insoluble polymers, which are insoluble in the gastrointestinal tract. Ethylcellulose is frequently used as a water-insoluble cellulose derivative coating. Aquacoat™ is an aqueous ethylcellulose pseudo-latex dispersion with a solids content of approximately 30%, which, aside from the polymer, contains the surfactants cetyl alcohol and sodium lauryl sulfate. Another commercially available ethylcellulose dispersion is Surelease™, in which ethylcellulose particles are stabilized with ammonium oleate. The Surelease™ dispersion also contains a plasticizer.

The use of aqueous polymer dispersions is much more complex than the use of organic polymer solutions. Several additives generally have to be added for the preparation or stabilization of the dispersion. Examples of the additives include surfactants, which stabilize the dispersion during preparation and storage; plasticizers, which lower the minimum film formation temperature; and preservatives, which protect the aqueous dispersion from microbial growth. These additives can affect the film formation and also the drug release behavior.

Aqueous polymer dispersions are generally also susceptible to physical and chemical damage. For example, the dispersions are sensitive towards temperature variations or high shear forces, which can lead to the flocculation of the dispersion, or sedimentation of the polymer particles. In addition, polymers, which are chemically degraded in water, cannot generally be used. Susceptibility to microbiological degradation or contamination is also a problem. The shelf life of aqueous polymer dispersions is therefore critical to acceptable performance. However, the shelf life is generally a maximum of one year.

For the above reasons, redispersible polymer powders, which are redispersed to form an aqueous polymer dispersion just prior to their application onto solid dosage forms have been prepared from several aqueous polymer dispersions. These redispersible polymer powders are generally prepared from aqueous polymer dispersions through drying processes such as spray drying. The advantages of these water-free redispersible polymers include improved storage stability, reduced transport and storage costs, and greater flexibility in the preparation of coating formulations.

With the redispersible polymer powders, it is important that the properties of the original polymer dispersions be retained after dispersion of the redispersible polymer powder in water. It is especially important that the original particle size distribution be retained because changes in the particle size distribution—for example, through the formation of agglomerates—can negatively affect the fusion of the particles (coalescence) in a homogeneous polymer film during coating.

Several redispersible polymer powders are commercially available. Aquateric™ is a spray-dried redispersible polymer powder made of cellulose acetate phthalate (CAP). CAP is, however, hydrolytically unstable. Prior to spray-drying the CAP, acetylated monoglycerides, which eliminate the coalescence of the polymer particles during drying and storage and which result in a good wetability of the redispersible polymer powders during redispersion, are added to the aqueous CAP-dispersion. Redispersible polymer powders containing polymers having ionizable functional groups (for example, carboxyl groups or ammonium groups) are also available. These polymers, which include, for example, spray-dried Eudragit™ L or RS 30 D, redisperse well because of their good wetability.

Presently, there are no redispersible polymer powders comprising water-insoluble polymers, such as nonionic polymers, which are commercially available for coating drugs. These polymers are primarily ethylcellulose and cellulose acetate. Although, aqueous polymer dispersions of these polymers can be converted into polymer powders through spray drying, the polymer powders are not redispersible. When these polymer powders are redispersed into an aqueous solution, they form larger agglomerates of particles such that the polymer dispersion does not retain its original particle size distribution. This agglomeration is due to the poor wetability of the water-insoluble polymers and the lack of stabilizing functional groups in the polymer. These larger polymer agglomerates lead to rapid sedimentation and result in an insufficient film formation during dosage form coating. Again, the particle size distribution of the redispersed polymer in solution is an important parameter. Generally, small particle sizes in the colloidal range are preferred for preparing films or coatings of acceptable quality.

Accordingly, a need exists for an improved method of dispersing redispersible polymer powders of nonionic polymers to form polymer dispersions which are suitable for coating dosage forms.

SUMMARY OF THE INVENTION

In the present invention, surprisingly, a good redispersibility of powders of nonionic polymers, which were prepared through spray- or freeze-drying of aqueous polymer dispersions, was obtained.

In one aspect, the invention provides a method of dispersing a redispersible polymer powder in an aqueous solution, wherein the redispersible polymer powder has been prepared by drying an aqueous polymer dispersion of a nonionic polymer, the method comprising the step of:

(a) adding the redispersible polymer powder to an aqueous solution containing an alkalinizing agent present in an amount sufficient to aid in the dispersion of the redispersible polymer powder to thereby form an aqueous dispersion of said redispersible polymer powder.

In one embodiment, the alkalinizing agent is a base, an alkaline substance, a buffer or a combination thereof. In another embodiment, the aqueous polymer dispersion containing the redispersible polymer powder further comprises an anionic surfactant, a cationic surfactant, a nonionic surfactant, sodium lauryl sulfate or a combination thereof In yet another embodiment, In yet another embodiment, the processes further comprises the step of:

(b) adding at least one of an anionic surfactant, a cationic surfactant, a nonionic surfactant, sodium lauryl sulfate and combinations thereof to the aqueous solution containing an alkalinizing agent.

Step (b) can be conducted before, during or after step (a).

In another aspect, the invention provides an aqueous dispersion of a redispersible polymer powder, wherein the aqueous dispersion has been prepared according to the above-described process.

Yet another aspect of the invention provides a dosage form coated with an aqueous dispersion of a redispersible polymer powder, wherein the aqueous dispersion has been prepared according to the above-described process.

Other features, advantages and embodiments of the invention will be apparent to those skilled in the art from the following description, examples and appended claims.

DETAILED DESCRIPTION OF THE INVENTION

The improved dispersion of redispersible polymer powders was generally achieved by adjusting the pH of the aqueous dispersion vehicle, i.e., the solution in which the powder was dispersed. The redispersibility of the redispersible polymer powder was significantly improved by addition of basic (alkalinizing) agents to the aqueous dispersion vehicle. The original aqueous dispersion, which is converted into the redispersible polymer powder through drying, is preferentially stabilised with one or more anionic surfactants, like sodium lauryl sulfate, cationic surfactants and/or nonionic surfactants. Surfactants are well known to those of ordinary skill in the art of pharmaceutical sciences, and all such surfactants are within the scope of the present invention. Such surfactants, however, may need to be added in different amounts to provide acceptable performance.

Alternatively, the pH of the polymer dispersion used to prepare the redispersible polymer powder can have a pH that has already been adjusted, for example, by the addition of bases or buffers, to improve dispersion of the redispersible polymer powder. In this instance, the pH of the aqueous solution used to disperse the redispersible polymer powder might not need to be adjusted again. In another alternative embodiment, the redispersible polymer powder is placed in water followed by adjustment of the pH of the water to an acceptable value thereby effecting dispersion of the redispersible polymer powder. The pH of the polymer dispersion prepared from the redispersible polymer powder will generally be greater than 3, preferably greater than 5, more preferably greater than 6. The pH of the redispersible polymer powder prior to redispersion in an aqueous solution can be adjusted according to the invention to at least 3, preferably at least 5, more preferably at least 6.

The particle size of the polymer dispersion and also of the redispersed polymer dispersion is preferably in the colloidal size range, which is preferably less than about 1 $\mu$m.

The redispersion of the redispersible polymer powder can be performed with any of a variety of commercially available mixing equipment known to those of ordinary skill in the pharmaceutical arts.

The redispersible polymer powder will generally comprise from about 0.05% weight to about 99.5% weight of a polymer dispersion made from the redispersible polymer powder.

The polymers which are suitable as redispersible polymer powders, according to the invention, include cellulose derivatives (for example, ethylcellulose, cellulose acetate, cellulose acetate butyrate, cellulose acetate propionate), acrylic derivatives (for example, poly (methylmethacrylates), cyanoacrylates) and also biocompatible and biodegradable polymers like poly(anhydrides), polyesters, poly(orthoesters), polyurethane, polycarbonate, polyphosphazene, and polyacetals. Specially preferred is ethylcellulose.

Examples of other compounds which can be added to the redispersible polymer powder include, for example, acacia, tragacanth, gelatin, starch, cellulose materials such as methyl cellulose, hydroxypropyl methylcellulose, microcrystalline cellulose and sodium carboxymethylcellulose, alginic acids and salts thereof, polyethylene glycol, guar gum, polysaccharide, sugars, invert sugars, poloxomers (PLURONIC™ F68, PLURONIC™ F127), collagen, albumin, gelatin, pregelatinized starch, anti-tacking agents such as talcum or magnesium stearate, fillers such as lactose and combinations of the above and the like.

As used herein, the term "alkalinizing agent" is intended to mean a compound that is generally known in the art to effect an increase in the pH of a solution to which is it added. Such compounds include, by way of example and without limitation, ammonia solution, ammonium carbonate, diethanolamine, monoethanolamine, potassium hydroxide, sodium borate, pH buffering agents, ammonium hydroxide, sodium carbonate, sodium hydroxide, triethanolamine, and trolamine and others known to those of ordinary skill in the art. As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and the like.

Various other additives such as plasticizers, pigments, or water-soluble polymers can be added to the polymer dispersion.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate ester-type plasticizers, triacetin, propylene glycol and glycerin.

Such plasticizers can also be ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co.

Pigments or coloring agents which are useful in the invention include titanium dioxide, and dyes suitable for food such as those known as F.D. & C. dyes and natural coloring agents such as grape skin extract, beet red powder, beta-carotene, annato, carmine, turmeric, and paprika.

Water-soluble polymers that are useful in the invention include hydroxypropyl methylcellulose, methylcellulose, poly(vinylpyrrolidone), and poly(ethyleneglycol).

An active ingredient can be incorporated into or adsorbed onto the polymer particles during or after the preparation of the aqueous polymer dispersion, so-called nanoparticles are prepared. After drying of the aqueous nanoparticle dispersion in a powder, this powder can then be redispersed with the known dispersion techniques.

As used herein, the term "active ingredient" is defined as a therapeutic agent, flavoring agent, a sweetening agent, a vitamin, a mineral and other such compounds for pharmaceutical applications.

The redispersed polymer powder can be used for the preparation of films, in particular, for the preparation of polymeric coatings.

The redispersibility of the dried powder was tested in diluted sodium hydroxide or HCl-solutions and water, and the pH-value of the resulting dispersion was measured. A significantly better redispersibility was obtained in the media with alkaline substances in comparison to water or media with acidic substances.

EXAMPLE 1

A 30% wt. ethylcellulose-dispersion (Aquacoat™) was dried to a redispersible polymer powder with a spray-dryer (Büchi 190). Alternatively, Aquacoat™ was dried in a freeze-dryer (alpha I-5, Christ GmbH, Osterode, Germany; drying temperature, −10° C. to −20° C., −48 h; secondary drying, 4 h at 20° C.) to form a redispersible polymer powder. An aqueous solution containing sodium hydroxide (0.001N NaOH) was then prepared. The redispersible polymer powder (15%w/v) was then added to the aqueous solution slowly while stirring or shaking. An aqueous polymer dispersion of acceptable quality was formed. The particle size distribution of the polymer after dispersion in the aqueous solution was substantially the same as it was as provided in the Aquacoa™ dispersion. The solids content of the supernatant was determined gravimetrically after predetermined time intervals and did not change significantly for the pH-adjusted dispersion while significant sedimentation was visible with the non-adjusted dispersion.

EXAMPLE 2

The following example compares the results obtained for coating a pellet with Aquacoat™ versus an aqueous dispersion of redispersible polymer powder made from ethylcellulose. Propranolol HCl-containing pellets were coated with Aquacoat™ (15% solids content, 25% triethyl citrate as plasticizer based on the polymer solids content of Aquacoat™) or with a redispersed ethylcellulose dispersion (15% solids content, 25% triethyl citrate as plasticizer based on the polymer solids content; the ethylcellulose was made from a redispersible polymer powder) to a 10% coating level. The coated pellets were then cured at 60° C. The redispersible polymer powder was prepared by spray-drying Aquacoat™ in a Buechi spray dryer. The redispersible ethylcellulose powder was then dispersed in 0.001 N NaOH in order to prepare the redispersed ethylcellulose dispersion. In order to compare the quality of the two different coats, the release of propanolol from the pellets was determined according to the USP XXIII guidelines, paddle method in pH 7.4 phosphate buffer. The difference in drug release between the two coated pellet formulations was insignificant demonstrating that a redispersible polymer powder processed according to the invention will retain substantially the same properties and performance as its source polymer had prior to being turned into a redispersible polymer powder.

The above is a detailed description of particular embodiments of the invention. Those of ordinary skill in the art should, in light of the present disclosure, appreciate that obvious modifications of the embodiments disclosed herein can be made without departing from the spirit and scope of the invention. All of the embodiments disclosed and claimed herein can be made and executed without undue experimentation in light of the present disclosure. The full scope of the invention is set out in the claims that follow and their equivalents. Accordingly, the claims and specification should not be construed to unduly narrow the full scope of protection to which the present invention is entitled.

We claim:

1. A method of dispersing a redispersible polymer powder in an aqueous solution, wherein the redispersible polymer powder has been prepared by drying an aqueous polymer dispersion of a nonionic polymer, the method comprising the step of:

(a) adding the redispersible polymer powder to an aqueous solution containing an alkalinizing agent present in an amount sufficient to aid in the dispersion of the redispersible polymer powder to thereby form an aqueous dispersion of said redispersible polymer powder.

2. A method according to claim 1, wherein the redispersible polymer powder has been prepared by one or more of spray-drying or freeze-drying of an aqueous polymer dispersion.

3. A method according to claim 1, wherein the nonionic polymer is a substantially water insoluble polymer.

4. A method according to claim 1, wherein the nonionic polymer in the aqueous polymer dispersion has a particle size primarily in the colloidal size range prior to drying.

5. A method according to claim 4, wherein the nonionic polymer of said redispersible polymer powder has a particle size primarily in the colloidal size range after the redispersible polymer powder has been dispersed in said aqueous solution containing an alkalinizing agent.

6. A method according to claim 1, wherein the alkalinizing agent is one or more of a base, an alkaline substance, a buffer and combinations thereof.

7. A method according to claim 1, wherein the aqueous polymer dispersion of said redispersible polymer powder further comprises one or more of an anionic surfactant, a cationic surfactant, a nonionic surfactant and combinations thereof.

8. A method according to claim 1, wherein the aqueous polymer dispersion of said redispersible polymer powder further comprises sodium lauryl sulfate.

9. A method according to claim 1, wherein the polymer is a cellulose derivative.

10. A method according to claim 9, wherein the polymer is selected from the group consisting of ethylcellulose, an ethylcellulose derivative, cellulose acetate and a cellulose acetate derivative.

11. A method according to claim 1, wherein the redispersible polymer powder comprises an active ingredient.

12. A method according to claim 1 further comprising the step of:

(b) adding at least one of an anionic surfactant, a cationic surfactant, a nonionic surfactant, sodium lauryl sulfate and combinations thereof to the aqueous solution containing an alkalinizing agent.

13. A method according to claim 12, wherein step (b) is conducted before, during or after step (a).

14. An aqueous dispersion of a redispersible polymer powder, wherein said dispersion has been prepared according to method of claim 1.

15. A solid dosage form coated with the aqueous dispersion of claim 14.

16. A method of dispersing a redispersible polymer powder in an aqueous solution, wherein the redispersible polymer powder has been prepared by drying an aqueous polymer dispersion of a pharmaceutically acceptable polymer, the method comprising the step of:

(a) adding the redispersible polymer powder to an aqueous solution containing an alkalinizing agent present in an amount sufficient to aid in the dispersion of the redispersible polymer powder to thereby form an aqueous dispersion of said redispersible polymer powder.

17. A method according to claim 16 further comprising the step of:

(b) adding at least one of an anionic surfactant, a cationic surfactant, a nonionic surfactant, sodium lauryl sulfate and combinations thereof to the aqueous solution containing an alkalinizing agent.

18. A method according to claim 17, wherein step (b) is conducted before, during or after step (a).

19. A method of improving the dispersion of a redispersible polymer powder into an aqueous solution, wherein the redispersible polymer powder has been prepared by drying an aqueous polymer dispersion of a pharmaceutically acceptable polymer, the method comprising one or more of the steps of:

(a) adding the redispersible polymer powder to an aqueous solution containing an alkalinizing agent present in an amount sufficient to aid in the dispersion of the redispersible polymer powder to thereby form an aqueous dispersion of said redispersible polymer powder; and (b) adding a sufficient amount of an alkalinizing agent to the aqueous dispersion of a pharmaceutically acceptable powder prior to drying the aqueous dispersion to form the redispersible polymer powder.

20. A method according to claim 19 further comprising one or more of the steps of:

(c) adding at least one of an anionic surfactant, a cationic surfactant, a nonionic surfactant, and combinations thereof to the aqueous solution containing an alkalinizing agent; and (d) adding at least one of an anionic surfactant, a cationic surfactant, a nonionic surfactant, and combinations thereof to the aqueous dispersion of a pharmaceutically acceptable powder prior to drying the aqueous dispersion to form the redispersible polymer powder.

* * * * *